(12) United States Patent
Yamaguchi et al.

(10) Patent No.: US 7,881,558 B2
(45) Date of Patent: Feb. 1, 2011

(54) SCANNING MICROSCOPE

(75) Inventors: Kohei Yamaguchi, Hitachinaka (JP); Kazuo Aoki, Hitachinaka (JP); Kenji Obara, Kawasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 113 days.

(21) Appl. No.: 12/420,263

(22) Filed: Apr. 8, 2009

(65) Prior Publication Data
US 2009/0202166 A1 Aug. 13, 2009

Related U.S. Application Data

(63) Continuation of application No. 11/411,154, filed on Apr. 26, 2006, now Pat. No. 7,526,143.

(30) Foreign Application Priority Data

Apr. 28, 2005 (JP) ............................. 2005-132677

(51) Int. Cl.
G06K 9/36 (2006.01)
(52) U.S. Cl. ........................ 382/276; 382/274; 382/275; 382/282
(58) Field of Classification Search ................. 382/260, 382/274, 275, 282, 284
See application file for complete search history.

(56) References Cited

U.S. PATENT DOCUMENTS

| | | | |
|---|---|---|---|
| 6,040,191 A | 3/2000 | Grow | |
| 6,750,968 B2 | 6/2004 | Sandusky | |
| 6,765,205 B2 | 7/2004 | Ochiai et al. | |
| 6,858,852 B2 | 2/2005 | Wolleschensky et al. | |
| 6,975,418 B1 * | 12/2005 | Ohta et al. | 358/1.15 |
| 6,982,811 B2 * | 1/2006 | Sato | 358/1.4 |
| 7,053,991 B2 | 5/2006 | Sandusky | |
| 7,287,253 B2 * | 10/2007 | Yamamura et al. | 717/176 |
| 7,359,535 B2 * | 4/2008 | Salla et al. | 382/128 |

FOREIGN PATENT DOCUMENTS

JP 2002-310962 A 10/2002

\* cited by examiner

*Primary Examiner*—Yosef Kassa
(74) *Attorney, Agent, or Firm*—McDermott Will & Emery LLP

(57) ABSTRACT

A method which, while displacing the field-of-view, allows the image in a target area to be acquired without degradations such as out-of-focus of the image. Plural pieces of images are acquired before and after a target area while displacing the field-of-view. Next, these images are grouped into groups each of which includes several pieces of images, and integrated images on each group basis are created. Moreover, a relational expression is calculated which holds between image displacement quantity calculated by comparing the integrated images with each other and the number of the photographed pieces of images. Furthermore, image displacement quantities between the acquired plural pieces of images are calculated from this relational expression. Finally, these images are corrected by the amounts of these displacement quantities, then being integrated. This process allows reconfiguration of the image in the target area.

9 Claims, 11 Drawing Sheets

: TARGET PHOTOGRAPHING AREA

: PHOTOGRAPHING RANGE (FIELD-OF-VIEW)

: STATE WHERE TARGET PHOTOGRAPHING AREA IS INCLUDED WITHIN PHOTOGRAPHING RANGE (FIELD-OF-VIEW)

SCANNING MICROSCOPE

RELATED APPLICATIONS

This application is a Continuation of application Ser. No. 11/411,154, filed Apr. 26, 2006, now U.S. Pat. No. 7,526,143 claiming priority of Japanese Application No. 2005-132677, filed Apr. 28, 2005, the entire contents of each of which are hereby incorporated by reference.

BACKGROUND OF THE INVENTION

1. Field of the Invention

The present invention relates to an imaging method. More particularly, it relates to an imaging method for performing image acquisition while displacing and without halting the field-of-view in an observation apparatus such as scanning electron microscope.

2. Description of the Related Art

A review apparatus has been known as an apparatus for observing in detail the foreign substances or defects on a semiconductor wafer. More concretely, this is the following apparatus: First, positions of the foreign substances or defects on the semiconductor wafer are identified in advance using some other apparatus (e.g., SEM or optical external-appearance inspection apparatus). Then, this wafer is displaced, and the defect locations on the wafer are observed based on the measured position information, thereby observing (i.e., reviewing) the detailed images. This review apparatus is mainly used for investigating the cause for occurrence of the foreign substances or defects, and for enhancing the yield in semiconductor-chip fabrication process. In the apparatus like this, it is required to inspect enormous number of wafers and enormous number of foreign substances or defects in a short time and with a high efficiency. This requirement further requires that the review apparatus itself eliminate wastes on the observation down to the lowest possible degree, and thereby execute the high-efficiency review. Hereinafter, in the present specification, the foreign substances or defects in general will be referred to as just "defects".

In the review apparatus, a stage on which the wafer is mounted is displaced up to the field-of-view center of the observation apparatus in an observation system, such as optical microscope or electron microscope. Next, the content that the observation system has photographed is stored and acquired into memory or storage device in a computer. Moreover, the images acquired are subjected to image processing, thus identifying accurate positions of the defects, and magnifying the accurate positions. Otherwise, the magnified images are acquired, thereby performing the detection and photographing of the defects. In order to detect a defect, in some cases, the stage is displaced to the position of the in-chip coordinate which is the same as that of the defect within a chip that is one-chip adjacent to the chip where the defect exists. Then, in this case, the review apparatus acquires an image for the comparison which is referred to as "reference image". At this time, usually, the stage is displaced to the image acquisition position, and there, the stage is halted, and then the image acquisition is performed. In the image acquired by the electron microscope or the like, which is accompanied by a comparatively bad S/N ratio, it is required to implement an enhancement in the S/N ratio by integrating plural pieces of images concerned therewith. If the image is acquired without halting the stage, the resultant image turns out to become a one which is blurred in the displacement direction. This situation, conventionally, has required that the review apparatus halt the stage at the image acquisition positions, and then acquire the plural pieces of images.

As a method of acquiring an image while displacing the stage, there has been known a one disclosed in JP-A-2002-310962. This method is as follows: First, displacement velocity of the stage is determined in advance. Then, the location to be scanned is changed in response to displacement quantity of the stage, so that the scan area will not displace even if the stage has been displaced.

In the method where the location to be scanned is changed in response to the displacement quantity of the stage, there are some cases where position coordinate of the stage and coordinate of the location at which the observation is actually performed do not necessarily coincide with each other. This phenomenon results from errors caused by physical factors of the stage, such as thermal deformation of the stage, height error of the measurement position, and error due to rigidity of the stage, and also the other factors such as the displacement and rotation of the wafer during the displacement of the stage. These errors attain to as much as 1 μm in some cases. Meanwhile, in recent years, significant development has been made in miniaturization of the defects to be detected. As a result, the observation at a high magnification is now becoming more and more required. For example, observing a defect of 45 nm or less requires that the field-of-view range of order of 1 μm be observed with a high definition. In this way, the higher the magnification becomes, the more incapable it becomes to neglect the errors as mention above. This situation makes it more difficult to irradiate one and the same location with the beam in accompaniment with the displacement of the field-of-view.

SUMMARY OF THE INVENTION

It is an object of the present invention to provide an imaging method which, during displacement of the field-of-view, allows the image in a target area to be acquired without degradations such as out-of-focus due to the image displacement.

In order to acquire a still image at a specific point during the displacement of the stage, in the present invention, displacement quantities, i.e., image shift quantities between respective images acquired during the stage displacement, are calculated from the acquired images. Next, the image shift quantities are corrected then to integrate the images, thereby performing reconfiguration of the image.

Namely, the imaging method according to the present invention includes the following steps: Acquiring plural pieces of specimen images while displacing a field-of-view on the specimen, grouping the plural pieces of specimen images into plural groups, each of the plural groups including plural pieces of specimen images which are continuously acquired, integrating the specimen images on each group basis, and thereby creating integrated images whose number is equal to the number of the groups, the specimen images belonging to each group, calculating image displacement quantity between the integrated images, determining a relationship between specimen-images acquisition time and the image displacement quantity from calculation result of the image displacement quantity, applying the determined relationship, and thereby calculating image displacement quantity for each of the plural pieces of specimen images, and making position corrections to the plural pieces of specimen images based on the calculated image displacement quantities, and after that, integrating the corrected specimen images thereby to reconfigure images.

At the step of determining the relationship between the specimen-images acquisition time and the image displacement quantity, the image displacement quantity can be determined as a function of the specimen-images acquisition time. The plural pieces of specimen images, typically, are acquired with a constant time interval.

According to the present invention, it becomes possible to acquire the image in a target range without completely halting the displacement of the field-of-view, and without degradations such as out-of-focus of the image.

Other objects, features and advantages of the invention will become apparent from the following description of the embodiments of the invention taken in conjunction with the accompanying drawings.

DESCRIPTION OF THE INVENTION

Figure 1:
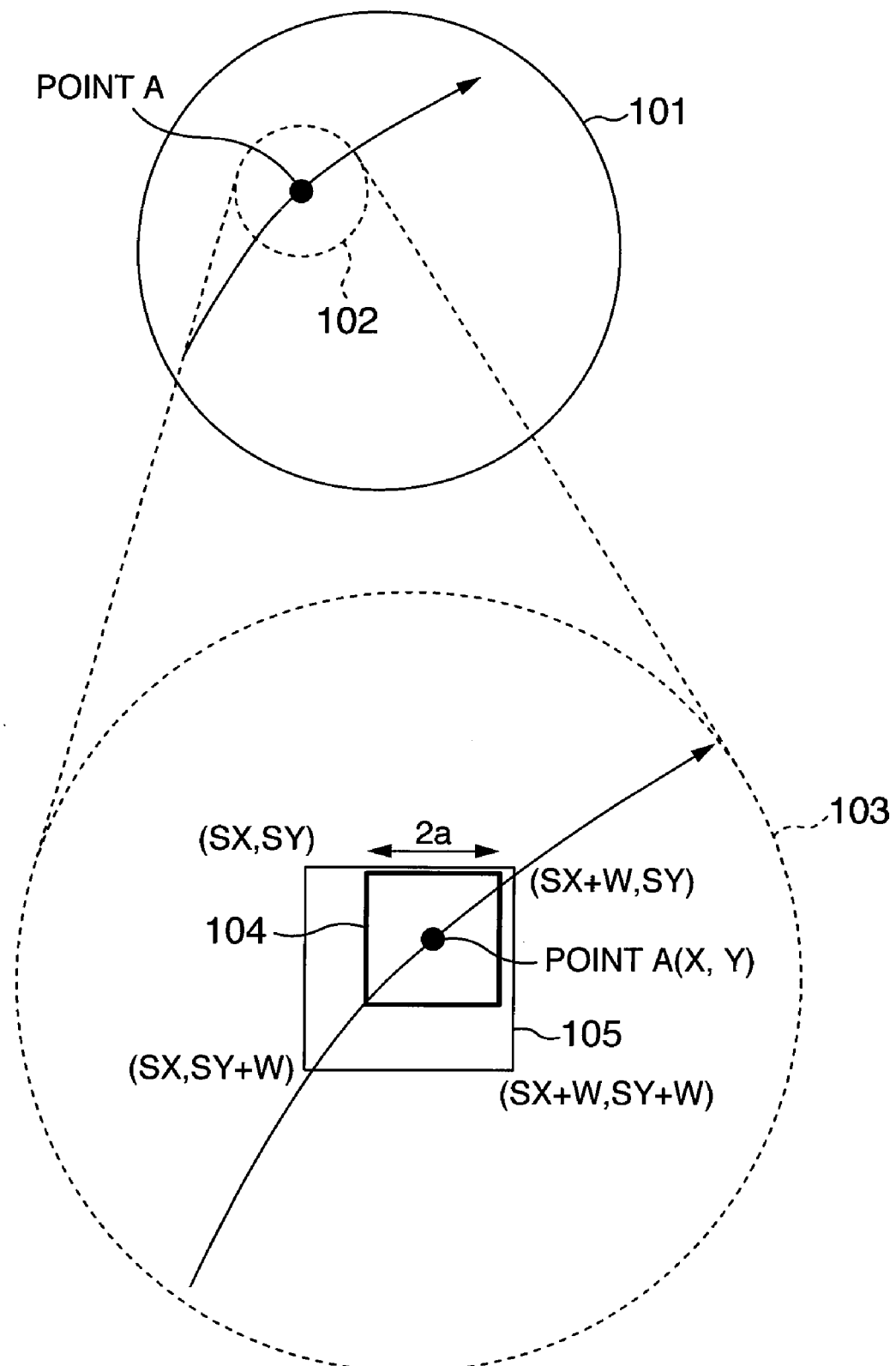
FIG. 1, which illustrates the principle of the present invention, is a plan view for explaining the manner in which field-of-view is displaced on a wafer.

Hereinafter, referring to the drawings, the explanation will be given below concerning embodiments of the present invention.

Figure 2:
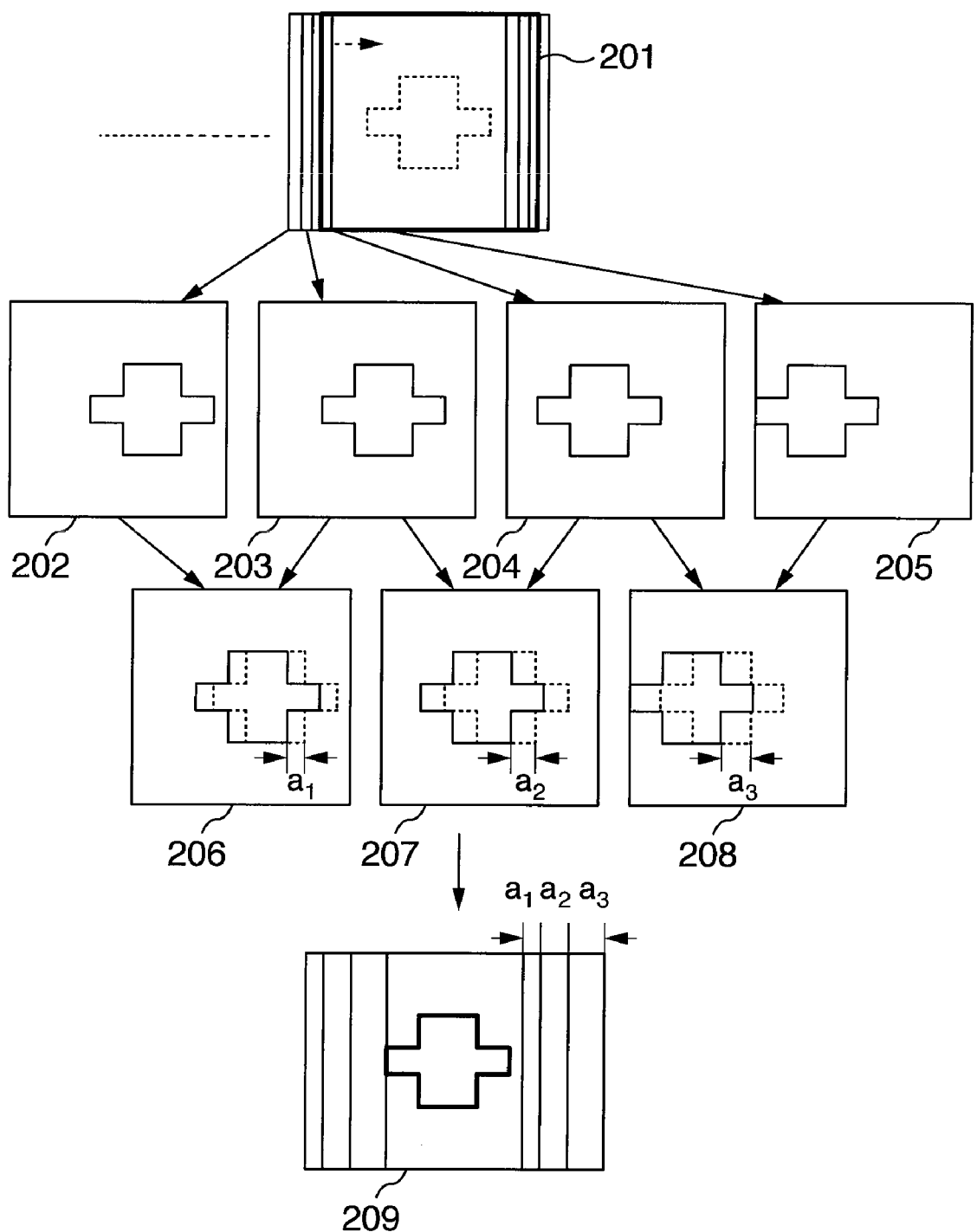
FIG. 2, which illustrates the principle of the present invention, is a diagram for explaining the method of acquiring plural pieces of images during displacement of the field-of-view, calculating image displacement quantities between the respective plural pieces of images, and correcting the images based on the calculated image displacement quantities, and integrating the corrected images.

FIG. 1 and FIG. 2 are diagrams for explaining the principle of the present invention. During displacement of the field-of-view indicated by an arrow in FIG. 1, when trying to acquire the image of a transversely and longitudinally 2a-wide range 104 with a point A existing on a wafer 101 set as the center, plural pieces of images of a range 105 which is wider than the range 104 are acquired before and after the point A. Then, image displacement quantities between the respective plural pieces of images are calculated from these images. Next, these images are shifted by the amounts of the calculated image displacement quantities, then being integrated thereby to reconfigure the image. This process allows the image in the target area to be acquired even while displacing the field-of-view. Incidentally, in FIG. 1, a range 103 is an enlarged view of a range 102.

Referring to FIG. 2, the explanation will be given below concerning the processing steps of the image reconfiguration. With respect to an image in size 201, plural pieces of images of this image are acquired while displacing the field-of-view. Reference numerals 202 to 205 denote the plural pieces of images thus acquired. Image displacement quantities a1, a2, and a3 between these images are calculated. As illustrated in 209, these images are shifted by the amounts of the calculated image displacement quantities, then being superimposed thereby to reconfigure the image. Images 206 to 208 are schematic diagrams for explaining the image displacement quantities, and indicate the case where the image is displacing in the horizontal direction for simplicity.

Figure 6:
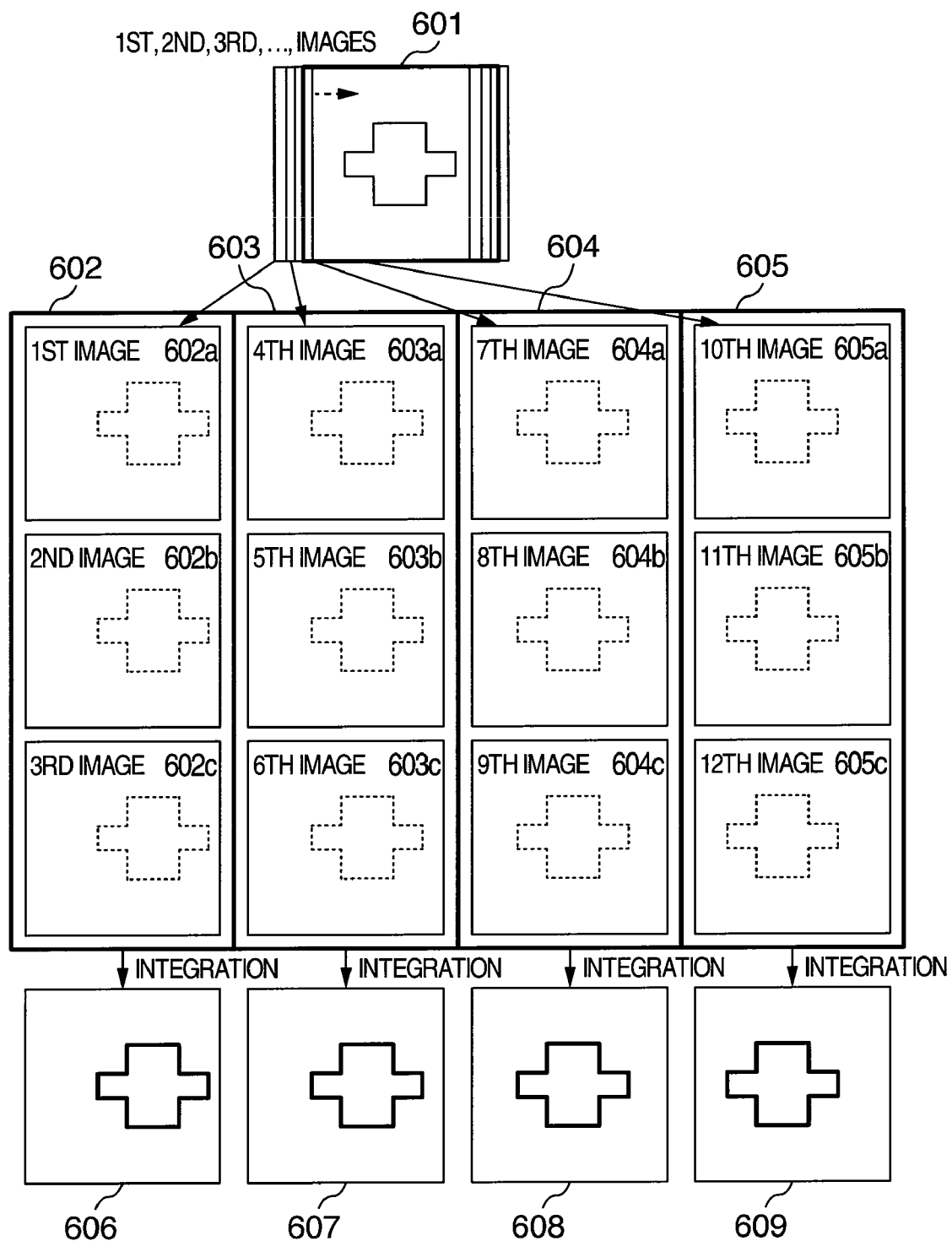
FIG. 6 is a diagram for explaining steps of grouping the images acquired during the displacement of the field-of-view into groups each of which includes several pieces of images, and creating integrated images on each group basis.

However, in the case where, like electron-microscope images, the S/N ratio per one-frame image (i.e., a single piece of image) is extremely bad, it is difficult to grasp configuration of the one-frame image. Accordingly, in many cases, it is difficult to calculate the image displacement quantities by merely comparing the one-frame images with each other. In view of this situation, as illustrated in FIG. 6, the acquired plural pieces of images (602a, 602b, 602c, 603a, . . . , 605b, 605c) are grouped into groups (602, 603, 604, and 605) each of which includes plural pieces of images. Moreover, integrated images (606, 607, 608, and 609) are directly created on each group basis. Furthermore, image displacement quantities are calculated based on the integrated images thus created. Although a certain extent of blurring due to the image displacement appears in each integrated image, the integration allows an enhancement in the S/N ratio. This makes it possible to obtain the picture quality which is satisfactory enough for the calculation of the image displacement quantities.

Figure 7A:
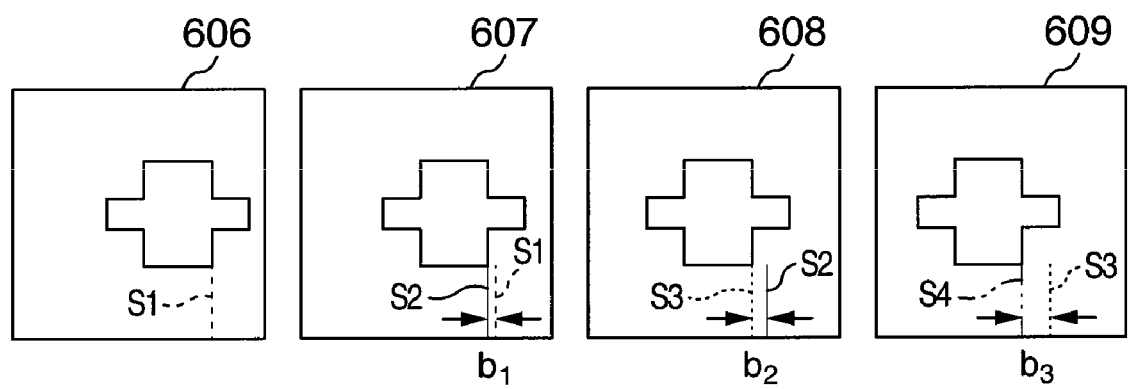
FIG. 7A and FIG. 7B are diagrams for explaining steps of calculating image displacement quantity between the integrated images, and calculating a relational expression which holds between the image displacement quantity and the number of the images.
Figure 7B:
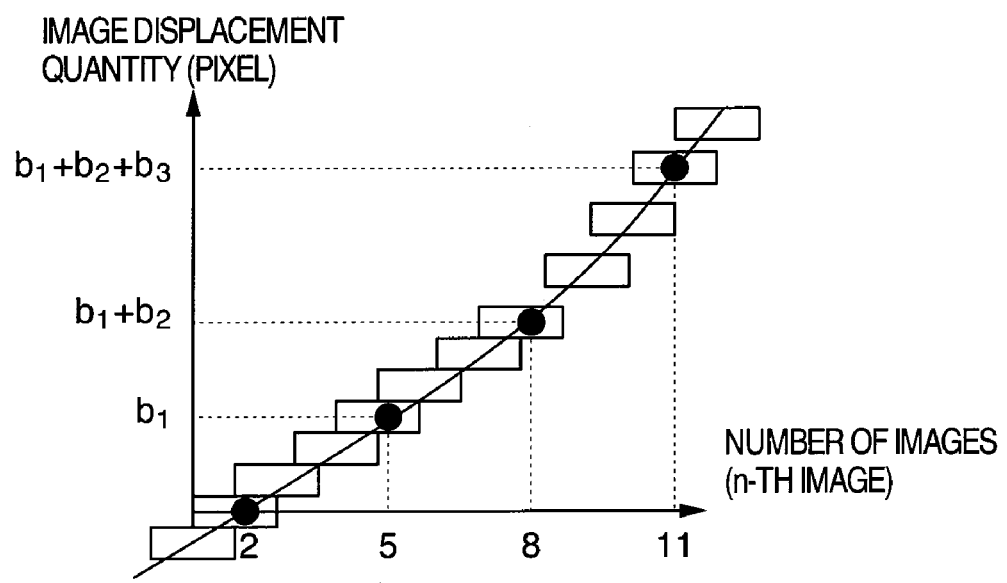

Once it has been found successful to calculate the image displacement quantity between the respective integrated images, a relational expression illustrated in FIG. 7B, which holds between the image displacement quantity and the number of the images acquired from an image acquisition start point-in-time, can be derived using methods such as the least squares method. In FIG. 7B, the transverse axis can also be interpreted as time. Taking advantage of this relational expression makes it possible to calculate the image displacement quantity for each of the plural pieces of images before the integrations. Consequently, these images are corrected by the amounts of the calculated image displacement quantities, then being integrated thereby to reconfigure the image. This process allows acquisition of the desired image.

In the case of this method, the image displacement quantities are calculated from the acquired images. This characteristic makes it unnecessary to determine in advance a tendency for the image shift. Also, this characteristic makes it possible to deal with the case as well where behavior of the image displacement varies because of various factors. Moreover, the image displacement quantities are calculated based on the integrated images created by integrating the images for each group including several pieces of images. This characteristic makes this method applicable to the case as well where the S/N ratio per a single piece of image is low like the electron-microscope images. Incidentally, as illustrated in FIG. 1, the area of the image after the reconfiguration becomes narrower than the acquired images. This situation requires that, unless a target area is acquired in a manner of being divided into plural times, the image in an area wider than the size of the necessary image be acquired in advance.

Hereinafter, the explanation will be given below concerning an embodiment of the case where the present invention is applied to the scanning electron microscope. Incidentally, the present invention is similarly applicable to microscopes using the other charge particles. Also, the present invention is similarly applicable to optical-type scanning microscopic optical systems such as laser-scanning cofocal microscope. Although the present invention itself is similarly applicable to ordinary optical systems (microscopic optical systems in particular), it is particularly effective to the case where the S/N ratio per a single piece of image is low like the electron-microscope images. Also, plural photographing apparatuses are usable in a manner of being combined with each other.

Embodiment 1

Figure 3:
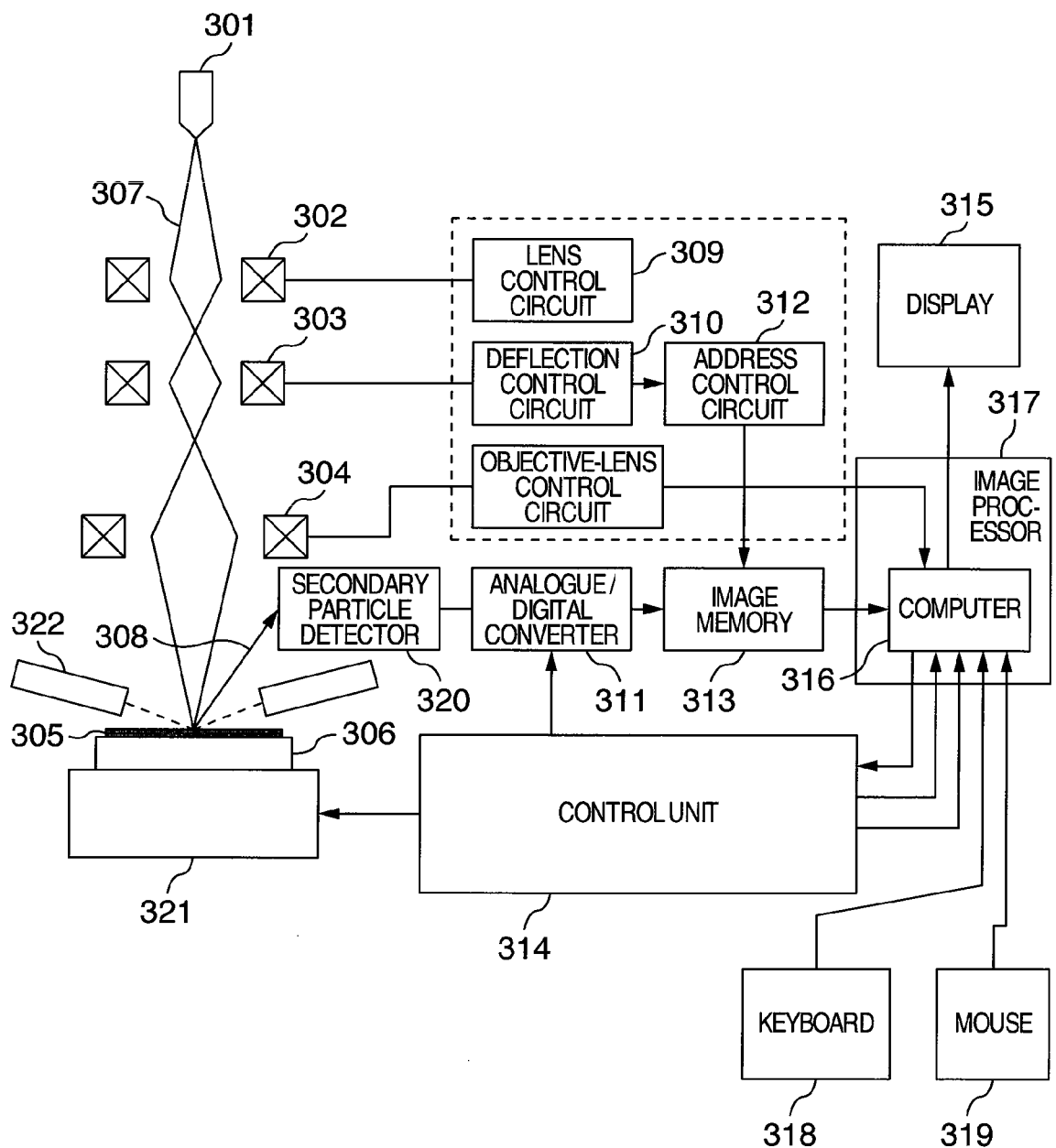
FIG. 3 is a longitudinal cross-sectional diagram for illustrating the main configuration of a scanning electron microscope.

FIG. 3 is a schematic view for illustrating the configuration example of a scanning electron microscope for acquiring an image according to the imaging method of the present invention. This scanning electron microscope includes configuration components such as an electron gun 301, an electron lens 302, a deflector 303, an objective lens 304, a specimen base 306, a lens control circuit 309, a deflection control circuit 310, a secondary particle detector 320, an A/D converter (Analog/Digital converter) 311, an address control circuit 312, an image memory 313, a control unit 314, a display 315, a computer 316, an image processor 317, a keyboard 318, a mouse 319, and a displacement stage 321. A reference numeral 322 denotes a height sensor. Incidentally, in the drawing, the illustration is omitted regarding a column for marinating the electron-optics system under vacuum.

An electron beam 307 emitted from the electron gun 301 is converged by the lens 302, then being scanned and deflected in a two-dimensional manner by the deflector 303. Next, the electron beam is converged by the objective lens 304, thereby being irradiated onto a specimen 305. What is referred to as "the objective lens" here may be not only of the magnetic field but also of the electrostatic type. Also, the objective lens may be replaced by some other mechanism as long as it is a mechanism for deflecting orbit of charged particles and converging the orbit onto the specimen surface.

Irradiating the specimen 305 with the electron beam 307 causes secondary particles 308 to occur, such as reflective electrons and secondary electrons in correspondence with configuration and material-quality of the specimen. Moreover, the secondary particles 308 are detected and amplified by the secondary particle detector 320, then being converted into digital values by the analogue/digital converter 311. The data converted into the digital values are stored into the image memory 313. As addresses for the image memory 313 at this time, the address control circuit 312 generates the addresses in synchronization with a scanning signal for the electron beam. Also, the image memory 313 transfers the stored SEM-image data to the image processor 317 at whatever time. Furthermore, the image processor 317 synthesizes the SEM-image data with screen data stored in a display memory of the computer 316, then displaying the synthesized data on the display 315 in real time. In addition thereto, the image processor also includes various image processings such as cut-out of an image and calculation of the displacement quantities, outputting the arithmetic-operation results (such as images and numerical data) to the computer 316.

The specimen 305 observed by the scanning electron microscope is supported by the specimen base 306. Also, the displacement stage 321 allows implementation of two-dimensional parallel displacement of the specimen base in accordance with a control signal from the control unit 314. This makes it possible to change the position at which the specimen 305 is scanned with the electron beam 307.

In the review SEM, the recorded data, such as coordinate values of defects acquired by some other apparatus, are read from the computer 316. Then, the coordinate data thus read are converted into stage-coordinate data of the review SEM itself. When displacing to locations of the defects, the stage is controlled using this stage-coordinate data, thereby displacing the wafer to the target locations. The stage coordinate can be measured in real time by a sensor using laser interferometer or the like. Incidentally, although, here, the stage displacement is employed as the method for displacing the field-of-view, some other mechanism is employable as long as it is capable of displacing the field-of-view with respect to the specimen such as the wafer.

Hereinafter, the explanation will be given below concerning an image acquisition sequence using the present invention. Incidentally, hereinafter, a square-shaped image will be considered in order to simplify the explanation. The configuration of the image, however, may be some other configuration such as rectangle. Now, consider the sequence where the image of the 2a-long square-shaped area 104 with the point A as the center will be finally outputted by passing through the route indicated by the arrow in FIG. 1, and acquiring the image during the displacement of the field-of-view.

Figure 4:
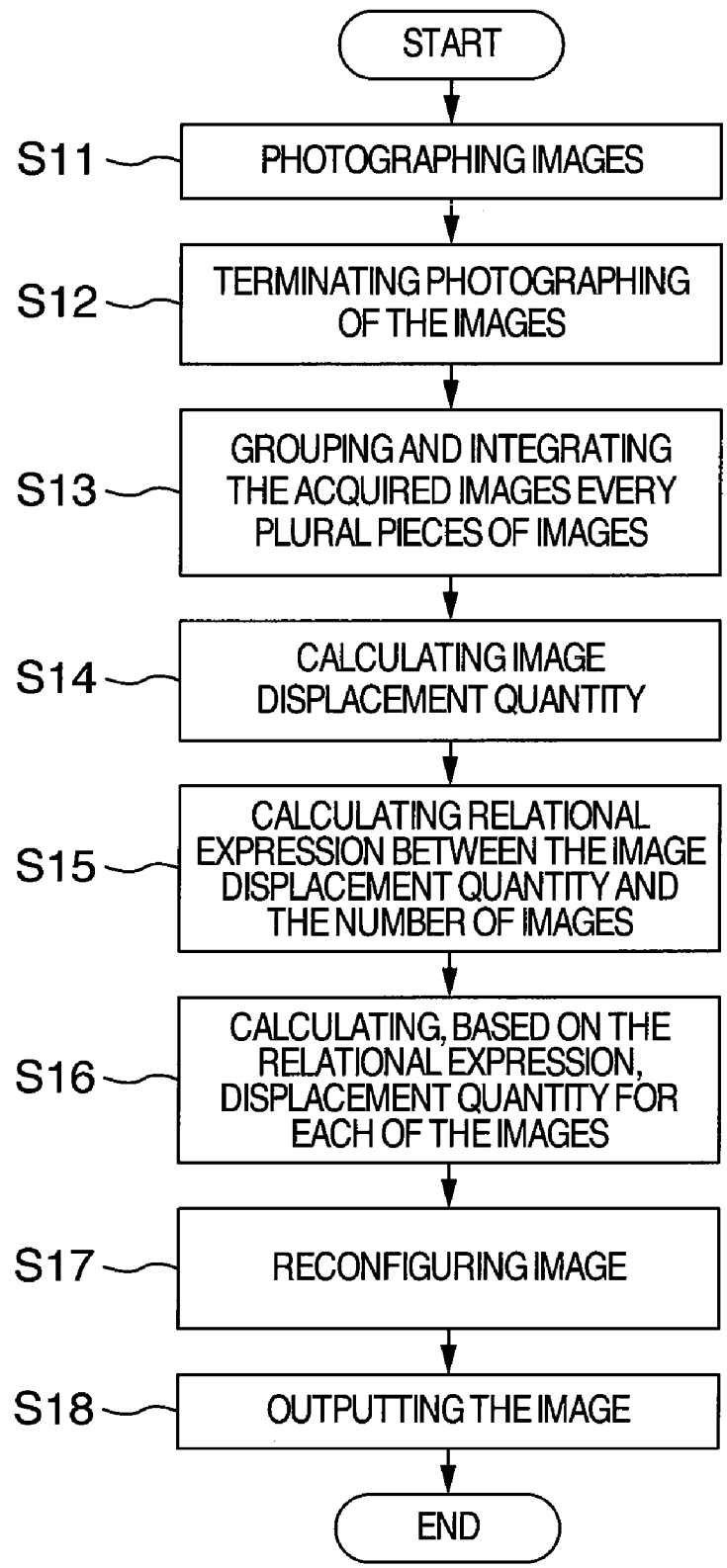
FIG. 4 is a flowchart for explaining image acquisition steps on the wafer.
Figure 5A:
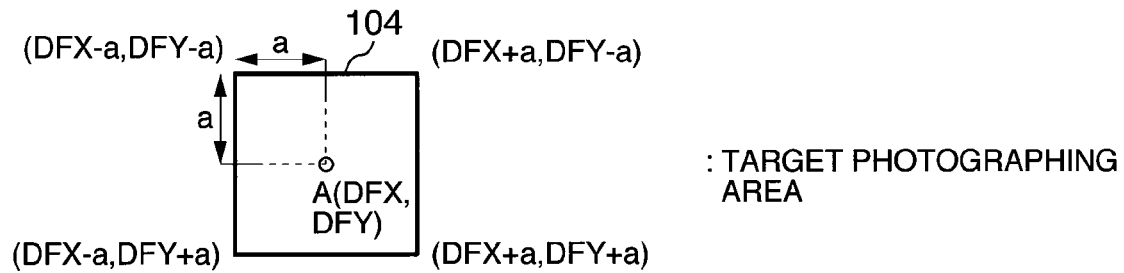
FIG. 5A to FIG. 5C are diagrams for explaining conditions under which an image acquisition area is included within the field-of-view.
Figure 5B:
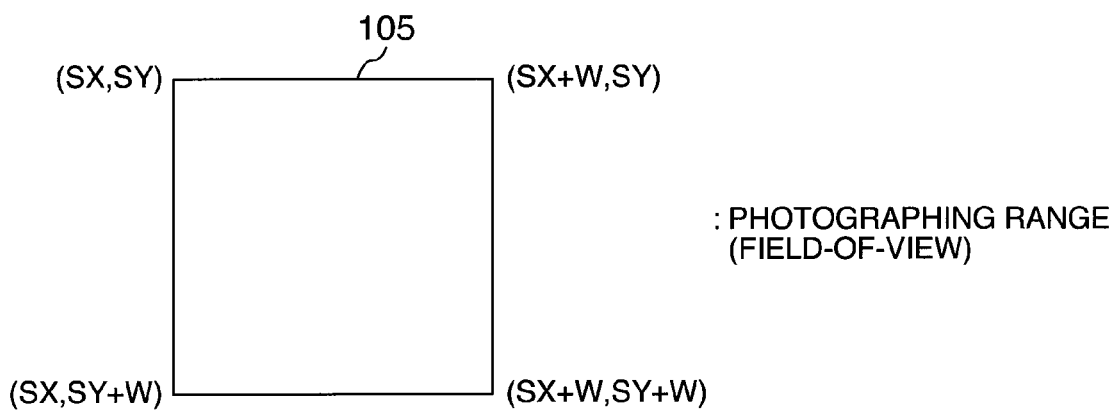
Figure 5C:
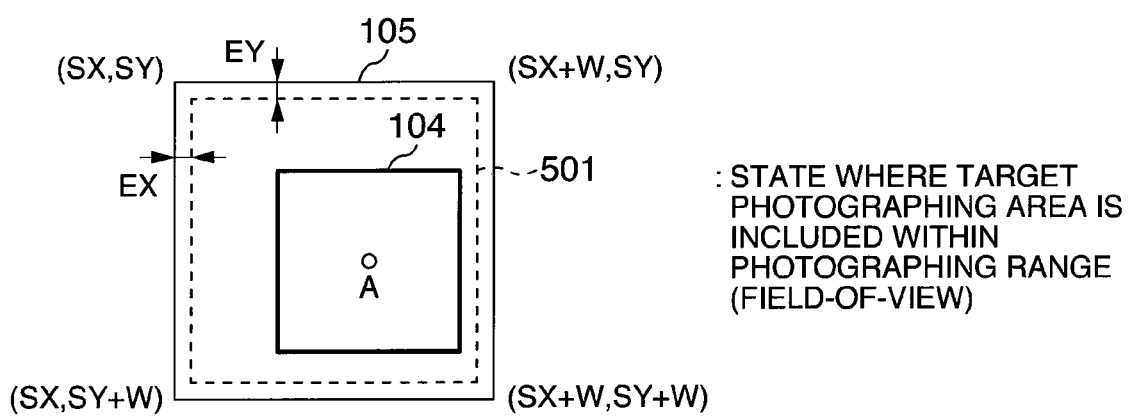

FIG. 4 illustrates a flowchart for the series of processings. At a step 11, the image acquisition is started from a point-in-time at which the target area 104 has been completely included in the image acquisition range by displacing the stage. Here, the size 105 of the image to be acquired is set to be larger than the size of the target area 104. This setting is needed for extracting image-overlapped portions at the time of reconfiguring the image later. For example, by acquiring the size 105 in a size which is two times as large as the area 104, it becomes possible to reconfigure the image even if the stage has been displaced by the amount of the size of the area 104. This size 105 can be modified depending on requirements. Also, a necessary size can be estimated when the stage displacement velocity can be predicted in advance. Also, the easiest method for setting the image acquisition range to be large enough is a method of enlarging the scanning range by the electron beam. This setting method, however, is not limited, e.g., setting plural photographing systems is also preferable. As illustrated in FIG. 5A to FIG. 5C, whether or not the entire target area 104 will be included within the image acquisition range 105 can be judged by confirming whether or not the following Expression (1) will be satisfied by the following parameters: The size W of the image acquisition range 105, stage coordinate (DFX, DFY) of the point A, and stage coordinate (SX, SY) of a point at the upper-left of the image acquisition range 105.

(Expression 1)

$$\begin{cases} SX \leq DFX - a \wedge DFX + a \leq SX + W \\ SY \geq DFY - a \wedge DFY + a \geq SY + W \end{cases} \quad (1)$$

$$\Leftrightarrow \begin{cases} SX + a \leq DFX \leq SX + W - a \\ SY + a \geq DFY \geq SY + W - a \end{cases}$$

Also, taking into consideration influences by factors such as error of the stage, a range which is narrower than the image acquisition range 105 is also settable as the condition. In the following Expression (2), defining the error amount as EX and EY, it is set as the condition that the target area 104 is included within a range 501. This is the case where the condition that the target area is included within an image acquisition range is made more severe. Determining the condition in this way makes it possible to prevent part of the target area 104 from lacking in the acquired images due to some reason or other. Incidentally, here, although the square-shaped area is assumed as the range 501 where the error amount is taken into consideration, the configuration of the area is of no importance and concern.

(Expression 2)

$$\begin{cases} SX + EX \leq DFX - a \wedge DFX + a \leq SX + W - EX \\ SY + EY \geq DFY - a \wedge DFY + a \geq SY + W - EY \end{cases} \quad (2)$$

$$\Leftrightarrow \begin{cases} SX + EX + a \leq DFX \leq SX - EX + W - a \\ SY + EY + a \geq DFY \geq SY - EY + W - a \end{cases}$$

Incidentally, it is allowable to acquire the images in an area which is smaller or larger in size than the ranges given by the Expressions (1) and (2). When displacing to the position of the point A in FIG. 1, depending on requirements, the stage displacement velocity is decelerated down to a degree needed for the image acquisition. The image acquisition will be continued with a constant time interval until the target area 104 has deviated from the image acquisition range 105 or the range 501, i.e., until the Expression (1) or (2) has been not satisfied. The image-acquisition time interval need not necessarily be the constant time interval. In that case, however, the image-acquisition time interval needs to be grasped by some parameter or expression such as displacement distance or displacement time. Here, the embodiment will be explained assuming that the image acquisition has been performed with the constant time interval.

The acquired plural pieces of images are sequentially transferred and stored into the image memory 313. After halting the image acquisition at a step 12, at a step 13, the acquired images are grouped into groups each of which includes plural pieces of images. Then, integrated images are created on each group basis. FIG. 6 is a diagram for explaining an example of this grouping. Here, the following example is indicated: The acquired images (602a, 602b, 602c, 603a, . . . , 605b, 605c) are grouped into the groups 602, 603, 604, and 605 each of which includes three pieces of images. Then, the grouped images are integrated on each group basis, thereby creating the integrated images 606, 607, 608, and 609. The grouping, however, is not limited thereto. Also, the number of the images within each group may be arbitrarily changed.

Next, at a step 14, image displacement quantities are calculated from the created integrated images 606, 607, 608, and 609. What are referred to as "image displacement quantities" here mean displacement distances by the amount of which the image has displaced within the field-of-view. Namely, the image displacement quantities refer to distances b1 to b3 in FIG. 7A and FIG. 7B. FIG. 7A illustrates an example of the case where the field-of-view is displaced in the horizontal direction. Selecting the position S1 of the integrated image 606 as the position reference, and assuming that the image has displaced up to the position S2 in the integrated image 607, the distance b1 equivalent to the difference therebetween turns out to become the image displacement quantity. Regarding the integrated images 608 and 609 as well, the image displacement quantities b2 and b3 are calculated assuming that the image has displaced up to the positions S3 and S4. There exist various calculation methods for calculating the image displacement quantity. For example, there exists the following method which uses the correlation coefficient: Namely, one of the two images is displaced by the amount (u, v), and the matching between the two images is performed. More concretely, letting F(X, Y) and G(X, Y) be the images, and letting n be the longitudinal (or transverse) length (unit: pixel) of the images, the correlation coefficient δ of the following Expression (3) will be calculated. Then, the amount (u, v) at the time when δ becomes its maximum will be calculated as the image displacement quantity.

(Expression 3)

$$\delta(u, v) = \frac{\sum_{X,Y}^{(n-u)(n-v)} FV(X, Y, u, v) \cdot GV(X, Y, u, v)}{\sqrt{\sum_{X,Y}^{(n-u)(n-v)} FV(X, Y, u, v)^2} \sqrt{\sum_{X,Y}^{(n-u)(n-v)} GV(X, Y, u, v)^2}}, \quad (3)$$

where $$FV(X, Y, u, v) = \{F(X, Y) - \overline{F(X, Y)_{u,v}}\}$$

$$GV(X, Y, u, v) = \{G(X - u, Y - v) - \overline{G(X - u, Y - v)_{u,v}}\}$$

$$\overline{F(X, Y)_{u,v}} = \sum_{X,Y}^{(n-u)(n-v)} \frac{F(X, Y)}{(n - u)(n - v)}$$

$$\overline{G(X - u, Y - v)_{u,v}} = \sum_{X,Y}^{(n-u)(n-v)} \frac{G(X, Y)}{(n - u)(n - v)}$$

Regarding the calculation of the image displacement quantity, it is allowable to use techniques other than this method. Next, at a step 15, from the calculated image displacement quantity, a relational expression will be calculated which holds between the image displacement quantity and the number of the images (or, elapsed time) from an image acquisition start point-in-time. Coefficients of a hypothesized relational expression will be calculated using the least squares method, assuming a graph where, as illustrated in FIG. 7B, the longitudinal axis represents the image displacement quantity and the transverse axis represents the number of the images (or, elapsed time) from the image acquisition start point-in-time. The coordinate of a group where the grouped images are integrated, i.e., the number of the images on the transverse axis in FIG. 7B, is determined to average the image acquisition orders in the group. How to take the coordinate is not limited to this method. An example of how to take the coordinate is such that the youngest order number in the group is defined as the image acquisition order of the group. In the case of the averaging method, a less error will occur even if the number of the images included in the group is changed. Hereinafter, as an example, the explanation will be given below concerning the case where the stage displacement velocity is decelerated with a constant deceleration. Letting an initial velocity be v, the acceleration be α, and time be t, the Expression for the velocity v(t) is given as follows:

(Expression 4)

$$v(t) = v - \alpha \cdot t \quad (4)$$

From this Expression (4), the stage displacement quantity x(n) from the image acquisition start point-in-time is given as follows: Here, n denotes the number of the images from the image acquisition start point-in-time.

(Expression 5)

$$x(t) = \int v(t)$$
$$= vt - \frac{1}{2}\alpha t^2$$
$$t \to n$$
$$x(n) = vn - \frac{1}{2}\alpha n^2 \quad (5)$$

It can be assumed that the above-described relational expression for the image displacement quantity will follow this Expression (5). The coefficients of this Expression (5) will be calculated using the least squares method from the data on the calculated image displacement quantity and the number of the images. This makes it possible to obtain the relational expression. The relational expression is not limited to the above-described expression, and thus some other expression may also be hypothesized. Also, the technique for determining the relational expression is not limited to this method either. Incidentally, in the case of using the least squares method, variance (i.e., error coefficient) associated with the hypothesized expression can be calculated. If, however, this variance value is found to be large, the case can be assumed where the displacement expression does not reflect on the actual circumstances. Accordingly, in this case, the stage is displaced to the location at which the image acquisition had been started, then performing the image acquisition once again. This makes it possible to prevent the necessary images from being missed. This step is not necessarily essential. Also, it is also possible to prepare plural expressions, and to employ an expression which leads to the smallest variance value, i.e., the expression with the least error. Additionally, here, only the displacement directed in one direction (i.e., the horizontal direction) is considered for simplifying the explanation. It is also allowable, however, to perform the same operation regarding plural directions, or to increase the variables thereby to deal with the plural directions simultaneously.

After having calculated the relational expression, the processing transfers to a step 16. Here, the shift quantities between the respective images (602a, 602b, 602c, 603a, . . . , 605b, 605c) before the grouping are calculated by taking advantage of the relational expression. In the case where the relational expression is the Expression (5), it can be shown that the n-th image is shifted from the (n−1)-th image by the amount of Δx(n) which is given by the following Expression (6):

(Expression 6)

$$\Delta x(n) = vn - \frac{1}{2}\alpha n^2 - \left(v(n-1) - \frac{1}{2}\alpha(n-1)^2\right)$$
$$= v - \frac{2n-1}{2}\cdot \alpha \quad (6)$$

At a step 17, based on the above-described shift quantities, it is calculated to which portion of the respective images the target area corresponds, and then the image is reconfigured. The explanation will be given below concerning this step by giving an example illustrated in FIG. 8, where reference numerals 801, 802, and 803 denote the acquired images whose one side is equal to W in size, and 804, 805, and 806 denote the ranges equivalent to the target area within the respective acquired images. Letting the coordinate of the point A within the first image 801 be (X1, Y1), and when letting the image displacement quantity within the second image 802 be (dx1, dy1), the coordinate of the point A within the second image 802 turns out to become (X1+dx1, Y1+dy1). Consequently, it turns out that the range 805 equivalent to the target area is given by the following Expression (7), and that this area will be cut out:

(Expression 7)

x:X1+dx1−a~X1+dx1+a y:Y1+dy1−a~Y1+dy1+a (7)

Hereinafter, basically the same processing is performed with respect to all the images, thereby creating the images. The cut-out Image group 807 is integrated by the image processor 317, thereby obtaining the target image 808. At a step 18, the reconfigured image is outputted to the display 315 via the computer 316, or is stored into the storage device inside the computer 316.

Figure 8:
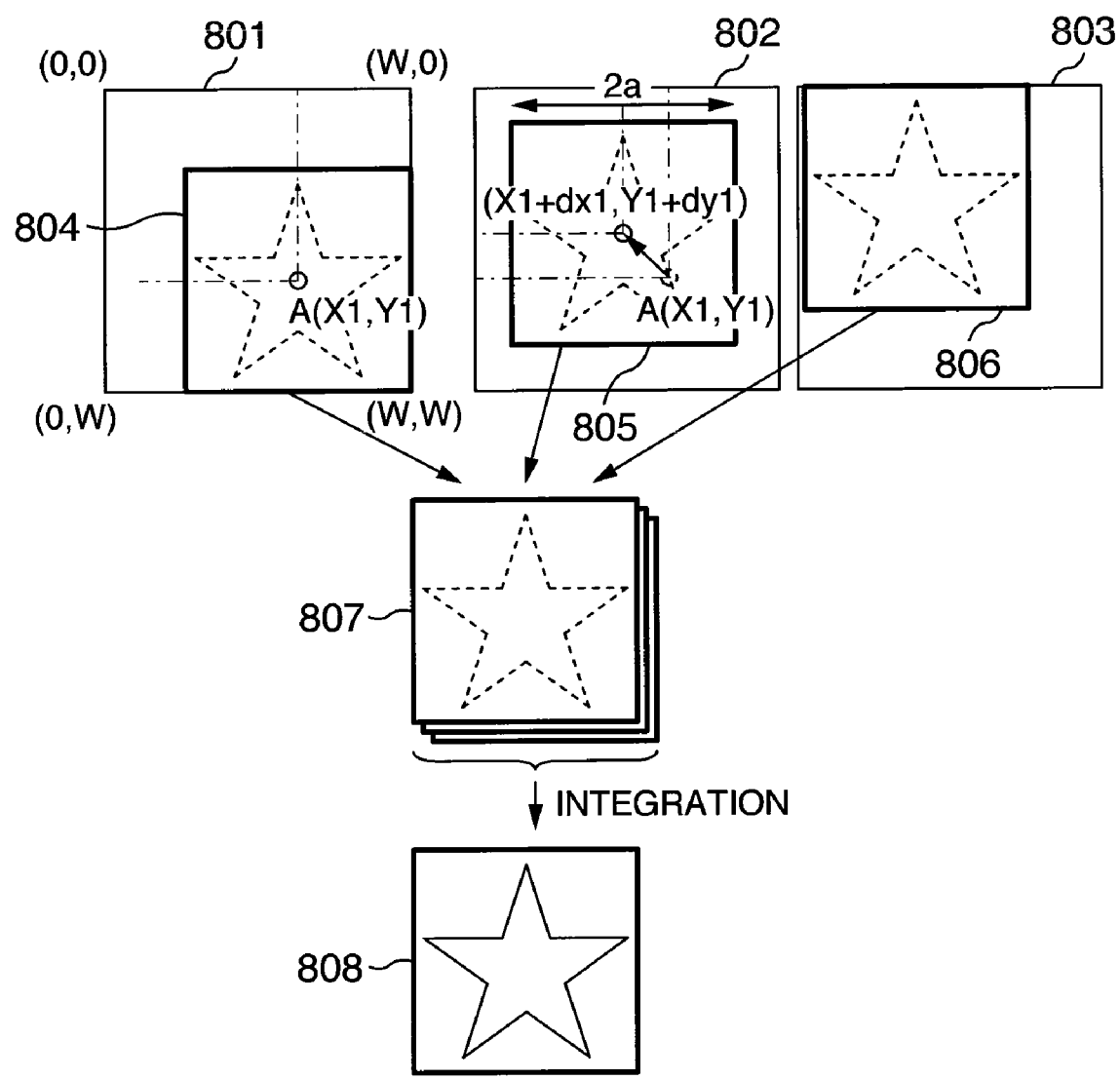
FIG. 8 is a diagram for explaining a method for calculating, from the calculated image displacement quantities, a portion corresponding to a target area within each image, and a method for reconfiguring the target area from the calculated image displacement quantities.
Figure 9:
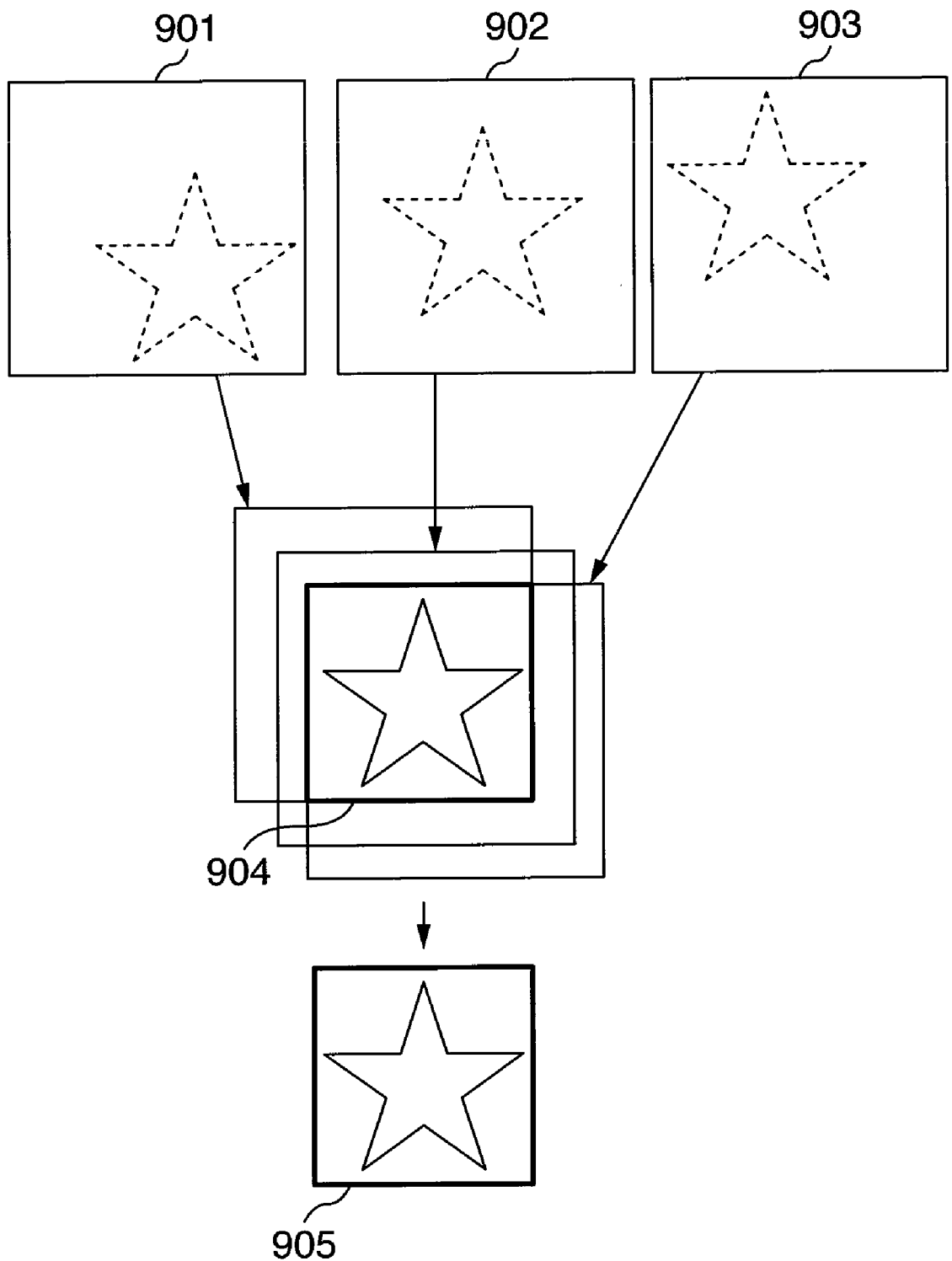
FIG. 9 is a diagram for explaining the method for reconfiguring the target area.

Other than the above-described method given by the flowchart mentioned in FIG. 8, the above-described processings, i.e., the image acquisition, the image grouping, the integration, the calculation of the image displacement quantity, the calculation of the image-displacement-quantity relational expression, the cut-out of the Images based on the image-displacement-quantity relational expression, the integration of the cut-out images, and the output of the reconfigured image, can be performed in parallel with each other on condition that these processings will not interfere with the stage displacement and with each processing. For example, in parallel with the image acquisition, already acquired images are grouped, then performing the integration operation and the calculation of the image displacement quantity. This method makes it possible to shorten the time needed from the photographing termination to the image output. Incidentally, here, the explanation has been given concerning the method where the ranges to be cut out are determined based on the displacement quantity for each image, and where the images are cut out and then integrated. As illustrated in FIG. 9, however, the following method is also allowable: Namely, the acquired images 901, 902, and 903 are shifted by the amount of the image displacement quantities, and then are integrated straightforwardly. Finally, the target portion 904 is cut out therefrom, then being outputted as the image 905.

Embodiment 2

Figure 11:
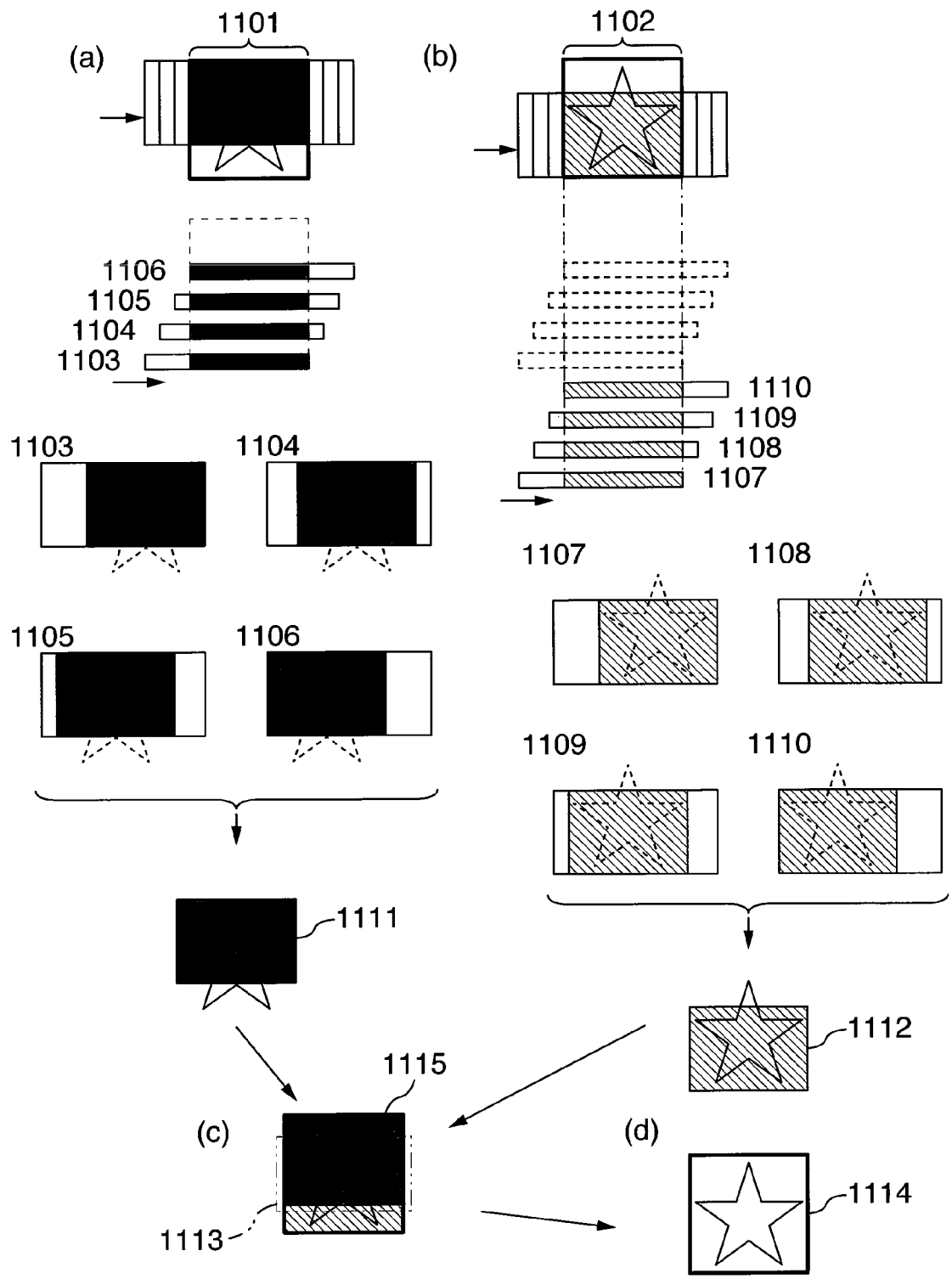
FIG. 11 is a diagram for explaining a method for acquiring images in a manner of being divided into plural times.

Next, the explanation will be given below concerning an embodiment where images are acquired by passing through one and the same observation area plural times, and where the reconfiguration is performed based on the images acquired in this way. For example, as illustrated in FIG. 11 (*a*), at first, images before and after an area 1101 are photographed in advance. After that, as illustrated in FIG. 11 (*b*), images before and after an area 1102 are photographed once again. Taking into consideration a processing step where both of the images will be finally connected with each other, the area 1101 is set such that the area 1101 overlaps with the area 1102 to some extant. The matching between the respective areas at the time of the connection is performed in this overlapped portion. After the image acquisition, as illustrated in FIG. 11 (*c*), the acquired images are reconfigured in each area. Then, the reconfigured images are connected with each other, thereby obtaining the target image. In the case of this embodiment, the photographing is executable even if the image acquisition range is not wider enough as compared with the target area. This characteristic makes it possible to prevent the degradation in the images due to enlargement of the scan range, thereby allowing the reconfiguration of the images.

Figure 10:
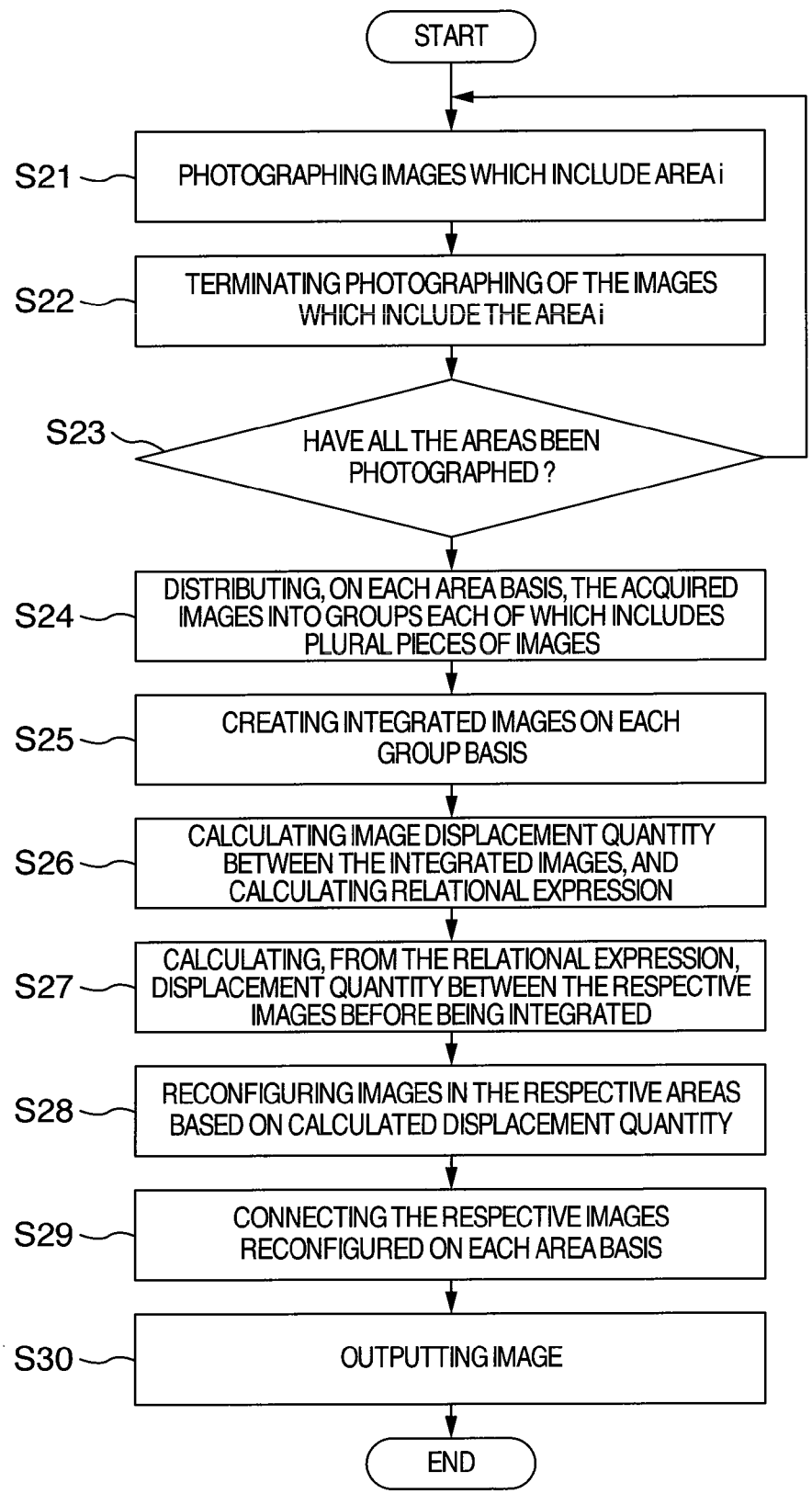
FIG. 10 is a flowchart for explaining the image acquisition steps on the wafer.

FIG. 10 illustrates a flowchart for the present embodiment. At a step 21, images before and after an area i are acquired. The reference notation i denotes numerals for area identification such as 1, 2, . . . . After having acquired the images including the area i at a step 22, the processing transfers to a step 23. Here, it is confirmed whether or not the image acquisition of all the areas has been terminated. In the present embodiment, in accordance with FIG. 11, consider the case of performing the image acquisition of the two areas 1101 and 1102. The step 21 and the step 22 are repeated until the acquisition of images needed for reconfiguring the areas 1101 and 1102 has been terminated. Incidentally, although the number and configuration of the areas and the number of the division are arbitrary, dividing the area into too many areas or assuming a complicated configuration therefor necessitates a considerable time for the image acquisition. Accordingly, it is desirable to divide the area into the least possible areas, and to set the configuration of each area to be a simple configuration such as rectangle. Also, it is desirable to provide the somewhat overlapped portion 1113 in each area as is illustrated in FIG. 11. As described above, this is performed in order to form the matching area at the time of connecting the areas with each other.

When the image acquisition regarding all the areas has been terminated, the processing transfers to a step 24 and a step 25. Here, on each area basis, the acquired images are distributed into groups each of which includes plural pieces of images. Moreover, integrated images are created on each group basis. This processing step can be performed in basically the same way as the corresponding one at the step 13 in the first embodiment, except that the processing step is performed on each area basis. Concerning calculation of image displacement quantity, calculation of relational expression, and image reconfiguration from a step 26 to a step 28, the processing steps themselves can also be performed in basically the same way as the corresponding portions from the step 14 to the step 17 in the first embodiment, except that the plural areas exist. Making reference to FIG. 11, these processing steps are equivalent to portions where an image 1111 is reconfigured from the integrated images 1103 to 1106, and that an image 1112 is reconfigured from the integrated images 1107 to 1110. Next, at a step 29, the created image 1111 and image 1112 in the respective areas are connected by being combined with each other, thereby completing the target image 1114. At the time of the connection, the respective image 1111 and image 1112 are connected by taking advantage of the mutually overlapped portion 1113 in a combined image 1115. Some other method is also usable as the connection method. Finally, a necessary portion is cut out from the connection-terminated image, then being outputted at a step 30.

The image acquisitions at the step 21 and the step 22, and the processings from the step 24 to the step 28 can be performed in parallel with each other in a range where these processings will not interfere with each other. Also, in the present embodiment, the image acquisition range is set as the configuration which differs from that of the target area, i.e., the rectangular area. This configuration, however, can be changed arbitrarily.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A scanning microscope for observing a specimen, comprising:
   an image acquisition section comprising a detector and control configured for acquiring plural pieces of specimen images while displacing a field-of-view on said specimen; and
   an image processor configured for grouping said plural pieces of specimen images into plural groups, each of said plural groups including plural pieces of specimen images which are continuously acquired, and integrating said specimen images for each group, thereby creating integrated images,
   the image processor comprising a computer configured for calculating image displacement quantity between said integrated images, determining a relationship between specimen-images acquisition time and said image displacement quantity, applying said determined relationship to calculate image displacement quantity for each of said plural pieces of specimen images, making position corrections to said plural pieces of specimen images based on calculated image displacement quantities, and integrating said corrected specimen images to configure a specimen image.

2. The scanning microscope according to claim 1, wherein said computing unit is configured for determining said image displacement quantity as a function of said specimen-images acquisition time when determining said relationship between said specimen-images acquisition time and said image displacement quantity.

3. The scanning microscope according to claim 1, wherein said plural pieces of specimen images are acquired with a constant time interval.

4. The scanning microscope according to claim 1, wherein said specimen images are output images of the scanning microscope.

5. The scanning microscope according to claim 1, wherein an acquisition range of said specimen images differs form a range of said specimen image after being configured.

6. The scanning microscope according to claim 1, wherein said computing unit is configured for cutting out a target area from said respective specimen images, and integrating said plural partial areas cut out, when making said position corrections to said plural pieces of specimen images and integrating said corrected specimen images to configure said specimen image.

7. The scanning microscope according to claim 1, wherein the computing unit is configured for shifting the specimen images by the amount of their displacement quantities to integrate said respective specimen images, and cutting out a target area, when making said position corrections to said plural pieces of specimen images and integrating said corrected specimen images thereby to reconfigure said specimen image.

8. The scanning microscope according to claim 1, further comprising a stage for supporting said specimen,
   wherein said image acquiring unit displaces the stage to perform said field-of-view displacement.

9. The scanning microscope according to claim 1, wherein:
   said image acquiring unit performs said field-of-view displacement in a first direction to obtain an partial image of a target area, and shifts said field-of-view in a second direction perpendicular to the first direction and perform said field-of-view displacement in the first direction to obtain another partial image of the target area, and the image processing and computing units utilize the partial images to configure the specimen image.

* * * * *